US012811004B2

(12) United States Patent
Shouldice et al.

(10) Patent No.: US 12,811,004 B2
(45) Date of Patent: Nov. 24, 2026

(54) AUTOMATIC USER INTERFACE IDENTIFICATION

(71) Applicant: ResMed Sensor Technologies Limited, Dublin (IE)

(72) Inventors: Redmond Shouldice, Dublin (IE); Graeme Lyon, Dublin (IE); Stephen McMahon, Dublin (IE); Roxana Tiron, Dublin (IE)

(73) Assignee: RESMED SENSOR TECHNOLOGIES LIMITED, Dublin (IE)

( * ) Notice: Subject to any disclaimer, the term of this patent is extended or adjusted under 35 U.S.C. 154(b) by 792 days.

(21) Appl. No.: 18/030,934

(22) PCT Filed: Oct. 8, 2021

(86) PCT No.: PCT/IB2021/059256

§ 371 (c)(1),
(2) Date: Apr. 7, 2023

(87) PCT Pub. No.: WO2022/074626

PCT Pub. Date: Apr. 14, 2022

(65) Prior Publication Data

US 2023/0377738 A1 Nov. 23, 2023

Related U.S. Application Data

(60) Provisional application No. 63/090,002, filed on Oct. 9, 2020.

(51) Int. Cl.
*G16H 40/63* (2018.01)
*A61M 16/00* (2006.01)
(Continued)

(52) U.S. Cl.
CPC ........ *G16H 40/63* (2018.01); *A61M 16/0069* (2014.02); *A61M 16/024* (2017.08);
(Continued)

(58) Field of Classification Search
None
See application file for complete search history.

(56) References Cited

U.S. PATENT DOCUMENTS 5,953,713 A * 9/1999 Behbehani .......... A61M 16/026 706/15
7,987,847 B2 * 8/2011 Wickham .............. A61M 16/00 128/204.26

(Continued)

FOREIGN PATENT DOCUMENTS

JP 2013514821 A 5/2013
JP 2020501804 A 1/2020

(Continued)

OTHER PUBLICATIONS

Dey et al., "ObSA: Automated detection of obstructive sleep apnea from ECG signals using CNN," Biomedical Engineering Letters, 2017. (Year: 2017).*

(Continued)

*Primary Examiner* — Manuel A Mendez
(74) *Attorney, Agent, or Firm* — NIXON PEABODY LLP

(57) ABSTRACT

Airflow parameters (e.g., flow rate and airflow pressure) of airflow generated by a flow generator of a respiratory therapy system can be measured during use and processed to automatically identify user interface and/or conduit identification information. This user interface and/or conduit identification information can be used to adjust settings of the respiratory therapy device, generate notifications (e.g., notifications of a detected change in user interface without concomitant, expected adjustment of settings of the respi-
(Continued)

ratory therapy device), or otherwise facilitate respiratory therapy of the user or of other users. User interface and/or conduit identification information can be indicative of specific characteristics of the user interface and/or conduit (e.g., resonant frequencies, impedance, and the like), a style of the user interface (e.g., a face mask, nasal mask, or nasal pillow) and/or style of conduit, a specific manufacturer, a specific model, or other such identifiable information.

21 Claims, 7 Drawing Sheets

(51) Int. Cl.

| | |
|---|---|
| ***A61M 16/06*** | (2006.01) |
| ***A61M 16/08*** | (2006.01) |
| ***G16H 10/20*** | (2018.01) |
| ***G16H 40/40*** | (2018.01) |

(52) U.S. Cl.

CPC ............ *A61M 16/06* (2013.01); *A61M 16/08* (2013.01); *G16H 10/20* (2018.01); *G16H 40/40* (2018.01); *A61M 2016/0027* (2013.01); *A61M 2016/0033* (2013.01); *A61M 2205/15* (2013.01); *A61M 2205/3306* (2013.01); *A61M 2205/3334* (2013.01); *A61M 2205/3365* (2013.01); *A61M 2205/3375* (2013.01); *A61M 2205/505* (2013.01); *A61M 2205/52* (2013.01); *A61M 2205/6018* (2013.01); *A61M 2230/42* (2013.01)

(56) References Cited

U.S. PATENT DOCUMENTS

| | | | |
|---|---|---|---|
| 8,677,997 | B2 | 3/2014 | O'Connor et al. |
| 2011/0232645 | A1 | 9/2011 | Smith |
| 2015/0224277 | A1 | 8/2015 | De Silva et al. |
| 2017/0266400 | A1 | 9/2017 | McCarthy et al. |

FOREIGN PATENT DOCUMENTS

| | | | | |
|---|---|---|---|---|
| WO | WO-9205439 | A1 * | 4/1992 | ............ G01N 29/12 |
| WO | WO-2011077274 | A1 * | 6/2011 | ........ A61M 16/0051 |
| WO | 2018/050913 | A1 | 3/2018 | |
| WO | 2021/176426 | A1 | 9/2021 | |

OTHER PUBLICATIONS

Efrat et al., Curve Matching, Time Warping, and Light Fields: New Algorithms for Computing Similarity between Curves, J Math Imaging Vis 27: 203-216, 2007. (Year: 2007).*

Lu et al., Pattern Recognition, Editorial / Pattern Recognition 75 (2018). (Year: 2018).*

JP 2020-501804 A translation (Year: 2020).*

JP 2013-514821 A translation (Year: 2013).*

International Search Report and Written Opinion in International Patent Application No. PCT/IB2021/059256 mailed Jan. 1, 2022 (15pp.).

Anonymous: "Cepstrum", Wikipedia. XP055875452; 16, Sep. 2020; Retrieved from the Internet: URL:https://en.wikipedia.org/w/index.php?title=Cepstrum&oldid=978651866 [retrieved on Dec. 22, 2021]; (8pp.).

* cited by examiner

AUTOMATIC USER INTERFACE IDENTIFICATION

CROSS REFERENCE TO RELATED APPLICATIONS

The present application claims the benefit of U.S. Provisional Patent Application No. 63/090,002 filed Oct. 9, 2020 and entitled "AUTOMATIC USER INTERFACE IDENTIFICATION," which is hereby incorporated by reference in its entirety.

TECHNICAL FIELD

The present disclosure relates to respiratory therapy devices generally and more specifically to automatic identification of user interfaces and conduits of respiratory devices.

BACKGROUND

Many individuals suffer from sleep-related respiratory disorders associated with one or more events that occur during sleep, such as, for example, snoring, an apnea, a hypopnea, a restless leg, a sleeping disorder, choking, an increased heart rate, labored breathing, an asthma attack, an epileptic episode, a seizure, or any combination thereof. These individuals are often treated using a respiratory therapy system (e.g., a continuous positive airway pressure (CPAP) system), which delivers pressurized air to aid in preventing the individual's airway from narrowing or collapsing during sleep. Pressurized air is delivered to the user via a user interface, such as a facial mask, a nasal mask, a nasal pillow mask, or the like. Different user interfaces can be used with the same respiratory device. Depending on the characteristics of the user interface, the respiratory device may need to be programmed or set up to achieve optimal results. Generally, one or more doctor visits may be needed to fit the respiratory system to the user.

SUMMARY

According to some implementations of the present disclosure, a method for automatically identifying a user interface includes generating airflow through a user interface. The method also includes measuring one or more airflow parameters associated with the generated airflow, wherein the one or more airflow parameters include at least one of a flow signal of the generated airflow over time and a pressure signal of the generated airflow over time. The method also includes identifying user interface identification information based on the measured one or more airflow parameters, wherein the user interface identification information is usable to identify a characteristic of the user interface.

The above summary is not intended to represent each implementation or every aspect of the present disclosure. Additional features and benefits of the present disclosure are apparent from the detailed description and figures set forth below.

Figure 1:
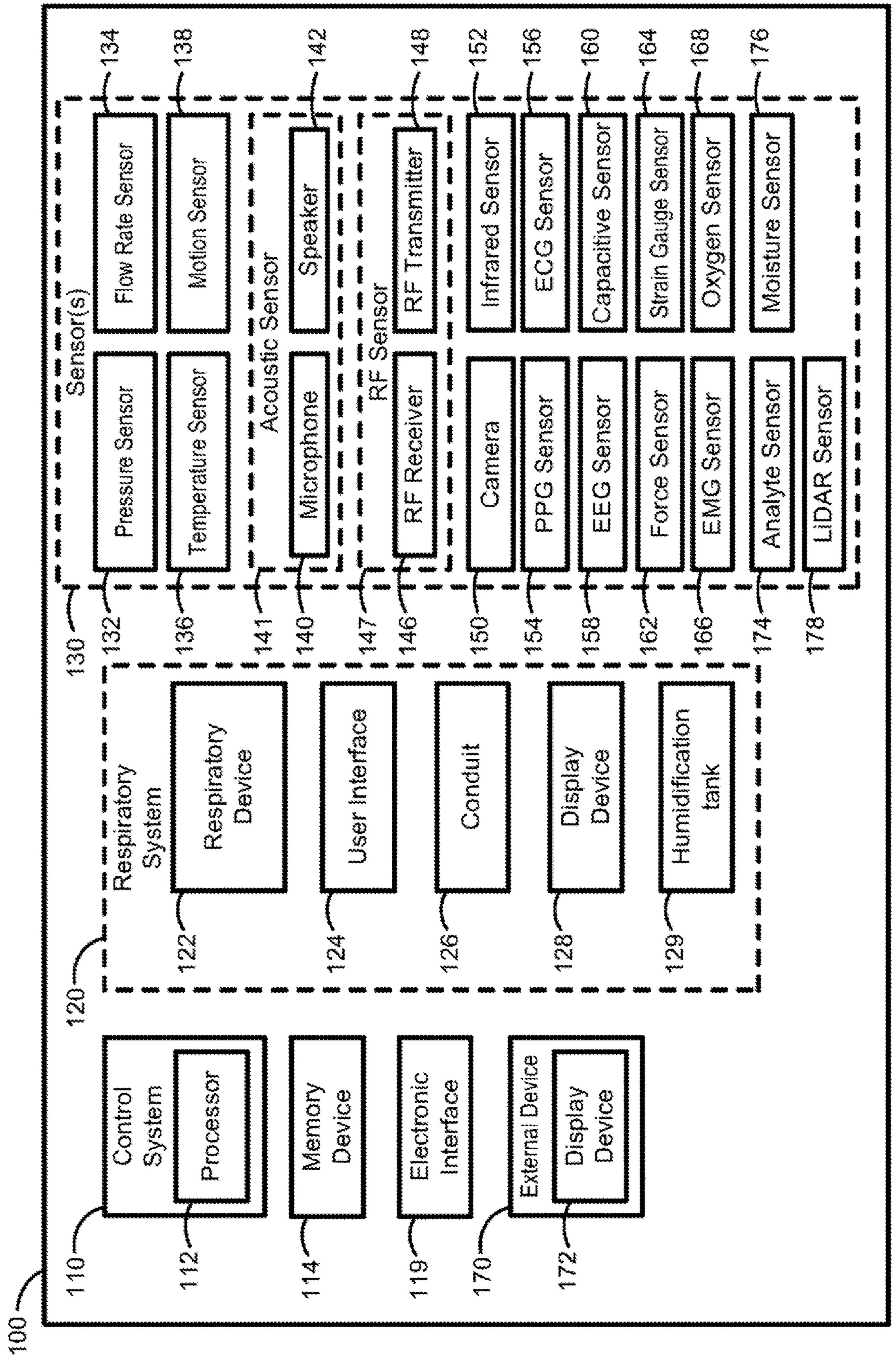
FIG. 1 is a functional block diagram of a system for generating physiological data associated with a user during a sleep session, according to certain aspects of the present disclosure.

While the present disclosure is susceptible to various modifications and alternative forms, specific implementations and aspects thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Certain aspects and features of the present disclosure relate to automatic detection of the user interface of a respiratory therapy system. Airflow parameters (e.g., flow rate and airflow pressure) of airflow generated by a flow generator can be measured during use and processed to identify user interface identification and/or conduit information. This user interface and/or conduit identification information can be used to adjust settings of the respiratory therapy device, generate notifications (e.g., notifications of a detected change in user interface without concomitant, expected adjustment of settings of the respiratory therapy device), or otherwise facilitate respiratory therapy of this or other users. User interface identification information can be indicative of specific characteristics of the user interface (e.g., resonant frequencies, impedance, and the like), a style of the user interface (e.g., a face mask, nasal mask, or nasal pillow), a specific manufacturer of the user interface, a specific model of the user interface, or other such identifiable information.

A respiratory therapy device can benefit from the knowledge of the user interface and/or conduit attached to it. Information about the user interface and/or conduit can be used to set internal parameters of the respiratory therapy device, as well as ensure correct reporting of data. With knowledge of the downstream system (e.g., the user interface and/or conduit connecting the user interface and respiratory therapy device), the respiratory therapy device can apply corrections to ensure correct therapy pressure is supplied to the user. User interface and/or conduit information can include information such as user interface and/or conduit manufacturer (e.g., brand), user interface and/or conduit model, user interface and/or conduit size, user interface vent presence and type, and the like.

While a user, or more likely a medical professional, can set up a respiratory therapy device to operate efficiently with a particular user interface and conduit, this setup process is prone to error. Additionally, even if properly set up, the user interface and/or conduit may be later switched out or replaced, or may even begin to operate differently due to normal wear and tear. If the respiratory therapy device is not properly updated accordingly with the correct user interface and conduit information, the proper respiratory therapy may not be provided to the user. As such, there is need for a respiratory therapy system that can automatically detect information about the user interface and/or conduit that is attached to the respiratory therapy device. Further, certain aspects of the present disclosure permit detection of the user interface and/or conduit without necessarily relying on external sensors or input from the user or medical professional.

Certain aspects of the present disclosure involve capturing airflow parameters, such as flow rate and pressure, over time as incoming data (e.g., airflow parameter data). This incoming data can be processed, such as through digital signal processing techniques, to generate a set of features that can be supplied to a machine learning model. The output of the machine learning model can be user interface identification information. This user interface identification information can be a particular user interface (e.g., a particular model of user interface), a general manufacturer of the user interface, a style of the user interface (e.g., facial mask, nasal mask, or nasal pillow), or other characteristics of the user interface. In some cases, incoming data can include additional information, such as a speed signal of the flow generator fan (e.g., revolutions per minute) or other characteristics of the flow generator or respiratory therapy device.

Features that can be determined from the incoming data can vary depending on implementation. In some cases, the style of user interface can be discerned from airflow parameter data. Other examples of features include presence of vents, number of vents, type of vents, occurrence of intentional leaks (e.g., vent flow), general shape of the user interface, general size of the user interface, breathing rate, inhalation volume, inhalation duration, exhalation volume, exhalation duration, occurrence of transient events, occurrence of unintentional air leaks, classification of an unintentional air leak, an indication of whether or not the user interface is being worn, frequency components (e.g., high frequency, middle frequency, and/or low frequency components of the airflow parameter data), and others. Any combination of these features can be used as input to a machine learning model to identify the user interface identification information.

For example, the presence of air leaks through a user's mouth may be indicative that the user interface being used is not a facial mask, but rather a nasal mask or nasal pillow. In another example, presence of both nasal breathing and mouth breathing can indicate that a facial mask is being used. In some cases, spectral components of the airflow parameters (whether generally or during certain stages of breathing, such as during inhale or exhale) can be used to indicate different shape and size features of the user interface. In another example, detection of intentional venting (e.g., via vents in the user interface) can be useful to determine user interface identification information, such as if intentional venting is detected from two vents and then later detected from a single vent, a determination can be made about the location of the two vents based on the ability for one to be temporarily blocked (e.g., when a user turns on their side during sleep). In another example, the system can calculate a relative vent flow by comparing measured flow to expected flow and allowing for any unintentional leaks (e.g., around the user interface seal). This relative vent flow can represent the vent's contribution to the flow, which can differ between user interfaces. For example, some vents exhibit flow that varies with pressure, while some vents exhibit constant flow despite changes in pressure.

Any suitable machine learning model can be used. In some cases, a machine learning model that is a deep neural network is used. In some cases, the deep neural network is a recurrent neural network, which can beneficially analyze airflow parameter data over time. In some cases, the recurrent neural network is a long short-term memory recurrent neural network. In some cases, the deep neural network is a convolutional neural network, which can be especially useful at analyzing graphical representations of the airflow parameter data (e.g., charts of flow rate and/or pressure over time, profile of the shape of one or more breaths, or a spectrogram of airflow parameter data).

In some cases, the system can make use of an expiratory pressure relief (EPR) mechanism. EPR can automatically reduce pressure for expiration to facilitate expiration by the user. In some cases, automatic identification of user interface identification information can make use of EPR information, such as whether or not EPR is activated and how much pressure is reduced and when. In some cases, EPR information can be determined directly from the airflow parameters. In some cases, however, EPR information can be obtained from one or more settings of the respiratory therapy device itself. In some cases, leveraging EPR information can be useful in analyzing airflow parameters, since some aspects of airflow parameters can change due to EPR. Thus, knowledge of EPR information can permit those changes to be filtered out, deemphasized, or otherwise handled to improve identification of user interface identification information.

In some cases, airflow parameter signals can be preprocessed to determine a signal to noise ratio to ensure adequate identification of user interface identification information can be obtained. In some cases, a signal to noise ratio can affect the confidence level of identified user interface identification information. For example, when the signal to noise ratio is low, the confidence level may also be low. In such cases, if the confidence level is below a threshold, no further action may be taken or a notice may be provided that the user interface identification information cannot be obtained.

In some cases, a respiratory therapy device can induce a known noise to calibrate the system. In some cases, the respiratory therapy device can induce a known change in airflow generation to evoke a detectable event in the airflow parameters. In some cases, existing detectable events can already exist in the airflow parameters (e.g., from user-based actions, such as donning or removing the user interface). These detectable event, whether intentionally created by the respiratory therapy device or naturally created by user action), can be used to help identify the user interface identification information through analysis of the airflow parameter data associated with the event. The airflow parameter data associated with the event can include airflow parameter data that occurs during the event, as well as airflow parameter data that occurs following the event, showing the system's response to the event.

Various actions can be taken based on the detected user interface identification information. In some cases, actions can include adjusting airflow generation of the respiratory therapy device, such as adjusting settings to improve efficiency of the respiratory therapy device or ensuring the respiratory therapy device supplies the correct therapy pressure to the user. In some cases, actions can include providing notices or notifications to the user or others (e.g., medical professionals or caretakers). In some cases, actions can include automatically deactivating the respiratory therapy device, such as if an unexpected, unauthorized, or dangerous user interface is detected (e.g., to enforce product recalls).

In some cases, settings of the respiratory therapy device can be adjusted dynamically based on identified characteristics of the identified user interface. In an example, the identified characteristic can be having one of two vents of the user interface being blocked (e.g., by a user sleeping on their side in a position that blocks one vent). In such an example, if the system automatically detects user interface identification information that indicates the user interface has two vents, but also detects that one of the vents is blocked, the system may dynamically update the settings of the respiratory therapy device such that the user is receiving the desired therapy despite one of the vents being blocked. Then, if the system later detects that the vent is no longer blocked, the settings of the respiratory therapy device can be reverted.

Aspects of the present disclosure are primarily described with reference to a user interface, such as automatic detection of a user interface and adjustments made to a respiratory therapy device based on a particular user interface. However, similar automatic detection and adjustments can be made with reference to other elements of the fluid delivery system, such as the flow generator generating the airflow and the conduit delivering the airflow to the user interface. The flow generator, conduit, and user interface can comprise a fluid delivery path from the flow generator to the user's airway. In some cases, additional elements can be included in the fluid delivery path. For the purposes of this disclosure, wherever aspects are described with reference to automatic detection of a user interface (e.g., identification of user interface identification information) and/or leveraging knowledge of the attached user interface (e.g., leveraging the user interface identification information), the same aspects can be used to automatically detect and leverage any single element or combination of elements making up the fluid delivery path, as appropriate.

In some cases, automatic detection (e.g., of the user interface and/or conduit) occurs continuously while the respiratory therapy device is in use. In some cases, automatic detection occurs occasionally (e.g., once every hour, every few hours, every day, every few days, every week, every few weeks, every month, every few months, every year, or every few years). In some cases, automatic detection occurs only once per sleep session or once per starting up the respiratory therapy device. In some cases, automatic detection occurs only after being manually initiated, such as by pressing a button or control associated with starting automatic detection of the user interface. In some cases, automatic detection occurs upon sensing that one or more components of the fluid delivery path has been removed, attached, or replaced.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure. The elements included in the illustrations herein may not be drawn to scale.

Referring to FIG. 1, a system 100 includes a control system 110, a respiratory therapy system 120, one or more sensors 130, and an external device 170. As described herein, the system 100 generally can be used to provide respiratory therapy to a user as well as automatically detect user interface identification information about the user interface 124 used in system 100.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the external device 170, a portion (e.g., a housing) of the respiratory system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the external device 170, within a housing of one or more of the sensors 130, or any combination thereof. Like the control system 110, the memory device 114 can be centralized (within one such housing) or decentralized (within two or more of such housings, which are physically distinct).

The electronic interface 119 is configured to receive data (e.g., physiological data, environmental data, airflow data, and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the external device 170. In other implementations, the electronic interface 119 is coupled to or integrated (e.g., in a housing) with the control system 110 and/or the memory device 114.

The respiratory system 120 (also referred to as a respiratory therapy system) includes a respiratory pressure therapy device 122 (also referred to herein as respiratory device 122), a user interface 124, a conduit 126 (also referred to as a tube or an air circuit), a display device 128, and optionally a humidification tank 129. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user. The respiratory device 122 can include a flow generator designed to generate the pressurized air (e.g., using one or more motors that drive one or more compressors or fans). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
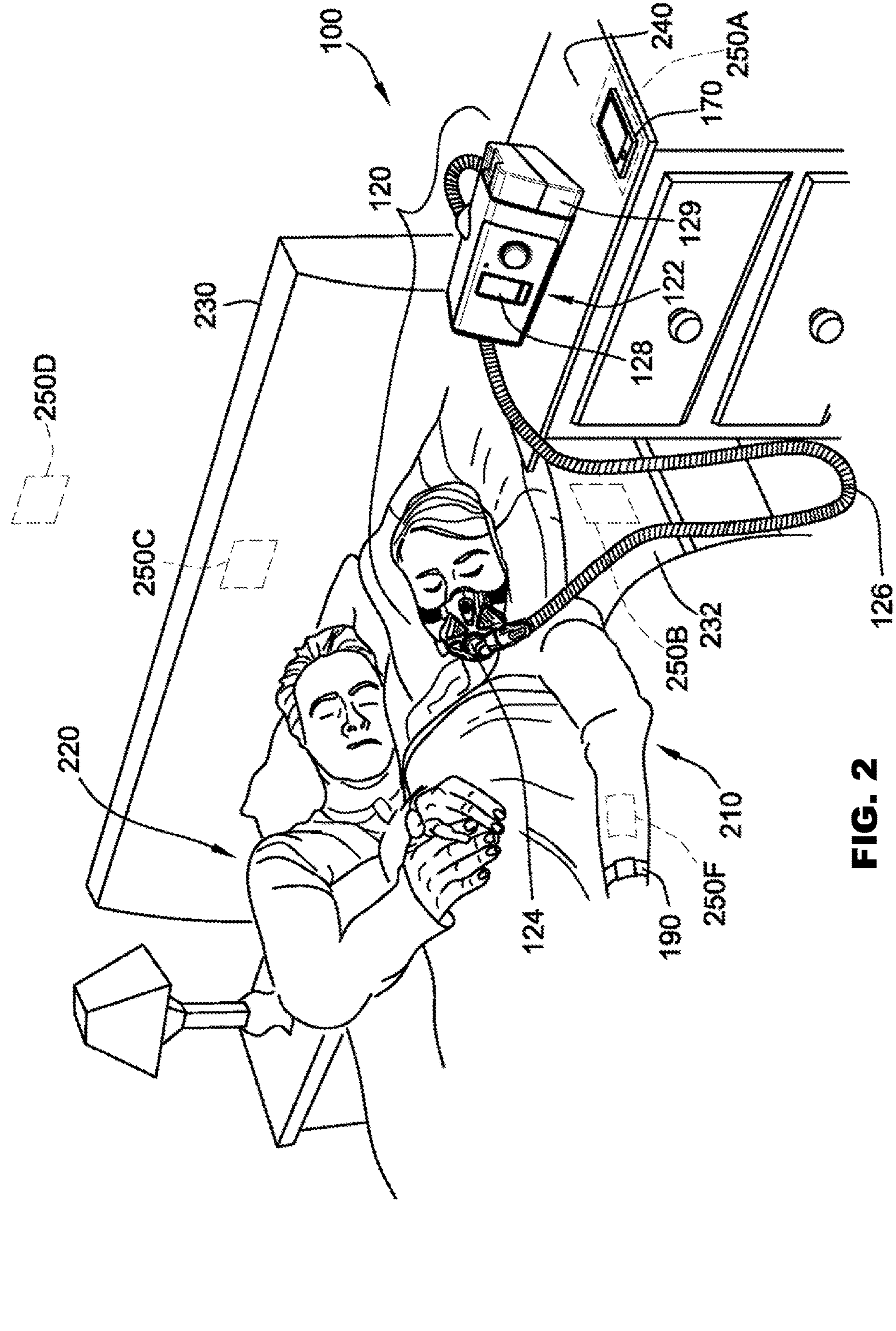
FIG. 2 is a perspective view of the system of FIG. 1, a user, and a bed partner, according to certain aspects of the present disclosure.

As shown in FIG. 2, in some implementations, the user interface 124 is a facial mask that covers the nose and mouth of the user. Other styles of user interfaces can be used. For example, in some cases, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 may be a tube-up mask (also known as a "top-of-head" tubing or mask, optionally wherein one or more straps of the headgear associated with the user interface may be configured to act as one or more conduits to deliver pressurized air to the full face or nasal user interface, and which user interface may be termed a "conduit mask." The user interface 124 can also include one or more vents for permitting the escape of carbon dioxide and other gases exhaled by the user 210. In other implementations, the user interface 124 can comprise a mouthpiece (e.g., a night guard mouthpiece molded to conform to the user's teeth, a mandibular repositioning device, and the like).

While user interface 124 depicted in FIG. 2 is a face mask style of user interface, other user interfaces can be used as part of a respiratory system 120. User interfaces of different models, of different styles, and from different manufacturers can be coupled to any given respiratory system 120, depending on the needs or desires of the user. Different user interfaces can have different characteristics about how it handles and responds to airflow. For example, different shapes of user interfaces can result in different impedance and different resonant frequencies within the respiratory airflow system 120. Thus, the respiratory device 122 (e.g., the fan or flow generator of the respiratory device 122) may need to be driven differently to generate the prescribed or desired airflow to the user's airway for different user interfaces. As used herein, the term "style" as used with reference to a user interface is intended to describe the type of user interface, such as full face mask, nasal mask, nasal pillow, mouthpiece, and the like. As used herein, the terms "model" and "manufacturer" as used with reference to a user interface are intended to indicate the common understanding of a model and manufacturer of any given user interface. Examples of models of user interface include F10 full face mask by ResMed™, a P10 nasal pillows mask by ResMed™, a N20 nasal mask by ResMed™, etc. User interfaces may be available from multiple manufacturers. A single manufacturer may make and distribute a number of different user interfaces across various models. Each model can have a particular style.

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation.

Like user interfaces, conduits of different styles, manufacturers, and models can be used with any given respiratory system 120. In some cases, different styles, manufacturers, and/or models of conduit can have different characteristics as to how the conduit responds to airflow. Thus, in some cases, it can be advantageous to have knowledge of the style, manufacturer, and/or model of conduit to ensure the proper settings are being used with the respiratory system 120.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure airflow parameters of pressurized air supplied by the respiratory device 122, such as air pressure and/or flow rate.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.), information about the user interface 124 (e.g., a style, manufacturer, model, or characteristic about the user interface 124), information about the conduit 126 (e.g., a style, manufacturer, model, or characteristic about the conduit 126), and/or other information (e.g., a sleep score or a therapy score (such as a myAir™ score), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory system 120 can be used, for example, as a ventilator or a positive airway pressure (PAP) system such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example, airflow data (e.g., data regarding airflow parameters, such as flow rate and pressure), physiological data, audio data, image data, other data, or any combination thereof. Airflow data can be used to determine user interface identification information and/or conduit identification information, as disclosed in further detail herein. In some cases, audio data, image data, and/or other data can be used to confirm or facilitate determination of user interface identification information and/or conduit identification information. For example, audio data or image data indicative of a particular shape or feature of a user interface can be used to facilitate determination of user interface identification information after being narrowed down through analysis of airflow parameters. Physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or any combination thereof. The sleep-wake signal can also be timestamped to indicate a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. Examples of the one or more sleep-related parameters that can be determined for the user during the sleep session based on the sleep-wake signal include a total time in bed, a total sleep time, a sleep onset latency, a wake-after-sleep-onset parameter, a sleep efficiency, a fragmentation index, or any combination thereof.

Physiological data and/or audio data generated by the one or more sensors 130 can also be used to determine a respiration signal associated with a user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, a number of events per hour, a pattern of events, pressure settings of the respiratory device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. In some cases, this respiration signal can be used to facilitate determination of user interface identification information and/or conduit identification information.

The pressure sensor 132 outputs pressure data (e.g., a pressure signal) that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122. The pressure sensor 132 can be, for example, a capacitive sensor, an electromagnetic sensor, a piezoelectric sensor, a strain-gauge sensor, an optical sensor, a potentiometric sensor, or any combination thereof. In one example, the pressure sensor 132 can be used to determine a blood pressure of a user.

The flow rate sensor 134 outputs flow rate data (e.g., a flow rate signal) that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The microphone 140 outputs audio data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory device 122, the use interface 124, the conduit 126, or the external device 170.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the audio data generated by the microphone 140 to the user. The speaker 142 can be coupled to or integrated in the respiratory device 122, the user interface 124, the conduit 126, or the external device 170.

The microphone 140 and the speaker 142 can be used as separate devices. In some implementations, the microphone 140 and the speaker 142 can be combined into an acoustic sensor 141, as described in, for example, WO 2018/050913, which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the external device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication can be WiFi, Bluetooth, or the like.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 210 enters the bed 230 (FIG. 2), and to determine a time when the user 210 exits the bed 230. In some cases, image data from the camera 150 can be used by the control system 110 to confirm or facilitate determination of user interface identification information and/or conduit identification information. For example, after narrowing down possible user interface identification information to a few possibilities through analysis of airflow parameters, image data can be requested (e.g., a photo of the user interface can be requested) and can be used to confirm or facilitate determination of the user interface identification information The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. In some cases, infrared data from the IR sensor 152 can be used to confirm or facilitate determination of user interface identification information and/or conduit identification information. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be coupled to or integrated in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 166 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles. In some cases, LiDAR data from the LiDAR sensor 178 can be used to confirm or facilitate determination of user interface identification information and/or conduit identification information.

While shown separately in FIG. 1, any combination of the one or more sensors 130 can be integrated in and/or coupled to any one or more of the components of the system 100, including the respiratory device 122, the user interface 124, the conduit 126, the humidification tank 129, the control system 110, the external device 170, or any combination thereof. For example, the microphone 140 and speaker 142 is integrated in and/or coupled to the external device 170 and the pressure sensor 130 and/or flow rate sensor 132 are integrated in and/or coupled to the respiratory device 122. In some implementations, at least one of the one or more sensors 130 is not coupled to the respiratory device 122, the control system 110, or the external device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

For example, as shown in FIG. 2, one or more of the sensors 130 can be located in a first position 250A on the nightstand 240 adjacent to the bed 230 and the user 210. Alternatively, one or more of the sensors 130 can be located in a second position 250B on and/or in the mattress 232 (e.g., the sensor is coupled to and/or integrated in the mattress 232). Further, one or more of the sensors 130 can be located in a third position 250C on the bed 230 (e.g., the secondary sensor(s) 140 is couple to and/or integrated in a headboard, a footboard, or other location on the frame of the bed 230). One or more of the sensors 130 can also be located in a fourth position 250D on a wall or ceiling that is generally adjacent to the bed 230 and/or the user 210. The one or more of the sensors 130 can also be located in a fifth position 250E such that the one or more of the sensors 130 is coupled to and/or positioned on and/or inside a housing of the respiratory device 122 of the respiratory system 120. Further, one or more of the sensors 130 can be located in a sixth position 250F such that the sensor is coupled to and/or positioned on the user 210 (e.g., the sensor(s) is embedded in or coupled to fabric or clothing worn by the user 210 during the sleep session). More generally, the one or more of the sensors 130 can be positioned at any suitable location relative to the user 210 such that the sensor(s) 140 can generate physiological data associated with the user 210 and/or the bed partner 220 during one or more sleep session.

Referring back to FIG. 1, the external device 170 includes a processor 172, a memory 174, and a display device 176. The external device 170 can be, for example, a mobile device such as a smart phone, a tablet, a laptop, or the like. The processor 172 is the same as, or similar to, the processor 112 of the control system 110. Likewise, the memory 174 is the same as, or similar to, the memory device 114 of the control system 110. The display device 176 is generally used to display image(s) including still images, video images, or both. In some implementations, the display device 176 acts as a human-machine interface (HMI) that includes a graphic user interface (GUI) configured to display the image(s) and an input interface. The display device 176 can be an LED display, an OLED display, an LCD display, or the like. The input interface can be, for example, a touchscreen or touch-sensitive substrate, a mouse, a keyboard, or any sensor system configured to sense inputs made by a human user interacting with the external device 170.

While the control system 110 and the memory device 114 are described and shown in FIG. 1 as being a separate and distinct component of the system 100, in some implementations, the control system 110 and/or the memory device 114 are integrated in the external device 170 and/or the respiratory device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for automatically determining user interface identification information. For example, a first alternative system includes the control system 110, the respiratory system 120, and at least one of the one or more sensors 130. As another example, a second alternative system includes the respiratory system 120, a plurality of the one or more sensors 130, and the external device 170. As yet another example, a third alternative system includes the control system 110 and a plurality of the one or more secondary sensors 140. Thus, various systems for determining sleep-related parameters associated with a sleep session can be formed using any portion or portions of the components shown and described herein and/or in combination with one or more other components.

Figure 3:
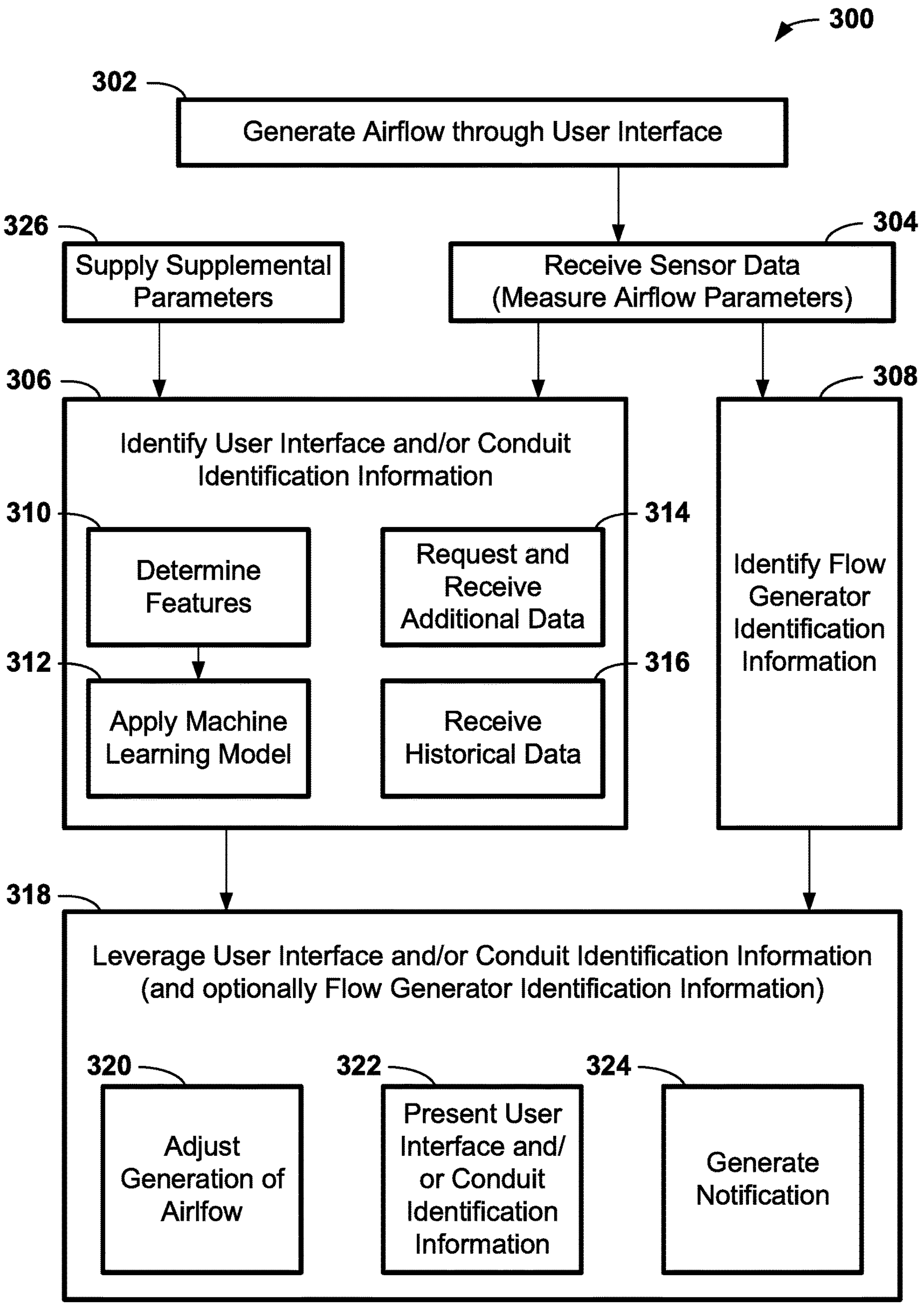
FIG. 3 is a flowchart depicting a process for analyzing airflow parameters to determine user interface and/or conduit identification information, according to certain aspects of the present disclosure.

FIG. 3 is a flowchart depicting a process 300 for analyzing airflow parameters to determine user interface and/or conduit identification information, according to certain aspects of the present disclosure. Process 300 can be performed on any suitable system, such as on control system 110 of system 100 of FIG. 1.

At block 302, airflow can be generated through a user interface (e.g., user interface 124 of FIG. 1). The airflow can be generated by a respiratory device, or more specifically, by a flow generator of a respiratory device. In some cases, the flow generator can operate with a particular set of settings or parameters. For example, a flow generator can include a fan that is driven at a certain speed or pattern of speeds.

In some cases, generating airflow at block 302 involves generating a known adjustment to the airflow (e.g., outside of normal operating procedures for respiratory therapy) and reverting the known adjustment to the airflow. Airflow parameters measured before, during, and/or after the adjustment can be used to determine user interface and/or conduit identification information. For example, in some cases, generating airflow at block 302 can involve inducing a short increase in the rate of airflow for the purposes of facilitating determination of the user interface and/or conduit identification information by detecting the adjustment and/or a response to the adjustment in the measured airflow parameters. For example, a fluctuation induced in flow rate and/or pressure can be generated, and the response to that generated fluctuation can be used to facilitate determination of the user interface and/or conduit identification information.

At block 304, sensor data can be received. Sensor data can be received from one or more sensors (e.g., one or more sensors 130 of FIG. 1). Receiving sensor data can include measuring airflow parameters of the airflow generated at block 302, such as flow rate, pressure, or both flow rate and pressure. In some cases, other parameters of the airflow can be measured at block 304. Measuring airflow parameters can include measuring airflow parameters over time, resulting in a signal indicative of the respective airflow parameter over time. For example, a flow rate signal can be indicative of the flow rate over time of the generated airflow from block 302. In another example, a pressure signal can be indicative of the pressure over time of the generated airflow from block 302.

In some cases, receiving sensor data at block 304 can additionally include receiving other sensor data, such as audio data, image data, physiological data, and the like. In some cases, receiving such other sensor data can be performed in response to a prompt given to a user, such as via a graphical user interface requesting additional data, as described below with reference to block 314. In some cases, receiving sensor data at block 304 can additionally include receiving sensed flow generator information, such as fan speed of the flow generator fan.

In some cases, receiving sensor data at block 304 can occur in real-time or approximate real-time with respect to when the sensor data was acquired. For example, in such cases, process 300 can be used to automatically determine user interface and/or conduit identification information (e.g., identify a user interface, a characteristic of a user interface, a conduit, a characteristic of a conduit, or any combination thereof) in real-time or approximate real-time. In other cases, however, receiving sensor data at block 304 can be asynchronously (e.g., asynchronous with acquiring the sensor data). In such cases, sensor data acquired by the system can be stored, such as in a memory, until such time as it is used to determine user interface and/or conduit identification information. For example, in such cases, airflow generated at block 302 can occur while the user is sleeping and making use of the system, at which time sensor data can be acquired and stored. At a later time, such as after the sleep session has ended, the system can receive the sensor data at block 304 and continue processing the sensor data to determine user interface and/or conduit identification information.

In some cases, receiving sensor data at block 304 includes receiving a first set of sensor data while the user is wearing the user interface and a second set of sensor data while the user is not wearing the user interface. In such cases, this sensor data (e.g., both the first set and the second set of sensor data) can be used to identify user interface and/or conduit identification information. Since different user interfaces may exhibit different changes in sensor data between when the user interface is worn and when the user interface is not worn, such data may be useful in facilitating identification of the user interface and/or conduit identification information.

In some cases, at optional block 326, supplemental parameters can be received and supplied for use during identification of the user interface and/or conduit identification information at block 306. Such supplemental parameters can include flow generator parameters and physiological data associated with the system. Flow generator parameters can include any parameters or other information associated with the flow generator or other parts of the respiratory system. Examples of flow generator parameters include presence of a humidifier, information about the humidifier (e.g., model or operational characteristics), inlet filter information (e.g., type, shape, or other characteristics), inlet baffle information (e.g., type, shape, or other characteristics), motor information (e.g., type, shape, or other characteristics of the motor of the flow generator), outlet baffle information (e.g., type, shape, or other characteristics), and expiratory pressure relief settings. Physiological data associated with the system can be any suitable physiological data separately determined by the system, such as central apnea detection information.

At block 306, user interface and/or conduit identification information can be identified using the received sensor data from block 304. Identifying the user interface and/or conduit identification information can include identifying user interface identification information, identifying conduit identification information, or identifying both user interface identification information and conduit identification information. Identifying user interface identification information can include identifying a particular user interface, a model of the user interface, a manufacturer of the user interface, a style of the user interface, or some other characteristic of the user interface. Identifying conduit identification information can include identifying a particular conduit, a model of the conduit, a manufacturer of the conduit, a style of the conduit (e.g., a shape of the conduit, a diameter of the conduit (e.g., 12 mm, 15 mm, or 19 mm inner diameter conduit), a length of the conduit, or the like), or some other characteristic of the conduit. Identification of the user interface and/or conduit identification information can occur through different techniques.

In some cases, identifying user interface and/or conduit identification information can include identifying a style of the user interface and/or conduit from a pool of possible user interface and/or conduit styles. In some cases, a broad determination of style of user interface and/or conduit can be quickly and readily determined from sensor data. After determining style of the user interface and/or conduit, other characteristics may be more easily determined from the sensor data. For example, after determining a style of the user interface and/or conduit, the system may be able to more easily determine a model and/or manufacturer of the user interface and/or conduit. For example, a different algorithm or model may be applied to sensor data from a nasal pillow user interface than that applied to sensor data from a facial mask user interface. In some cases, however, style of user interface and/or conduit need not be determined first or separately.

In some cases, identifying the user interface and/or conduit identification information can include applying, at block 312, a machine learning model to incoming data, such as the received sensor data from block 304. Any suitable machine learning model or algorithm can be used. In some cases, it may be especially useful to use a machine learning model that is a neural network model, such as a deep neural network. In some cases, use of a recurrent neural network model can be effective in identifying user interface and/or conduit identification information from input data, such as airflow parameter signals (e.g., a flow rate signal and a pressure signal). When a recurrent neural network is used, the recurrent neural network can be a long short-term memory recurrent neural network. In some cases, use of a convolutional neural network model can be effective in identifying user interface and/or conduit identification information from input data, such as plots of airflow parameters (e.g., flow rate plots and pressure plots). In some cases, a combination of multiple neural networks can be used.

In some cases, identifying the user interface and/or conduit identification information at block 306 can include generating a spectrogram using the airflow parameters and applying the spectrogram to a deep neural network (e.g., a convolutional neural network).

A machine learning model used at block 312 can be trained in advance. The machine learning model can be trained using appropriate training data for the input data used with the model. For example, in some cases, a machine learning model that receives a flow signal and a pressure signal and generates user interface and/or conduit identification information can be trained using a corpus of data containing flow signals, associated pressure signals, and associated user interface and/or conduit identification information. In some cases, the machine learning model is trained using a corpus of flow signal data and pressure signal data across a number of different user interfaces and/or conduits. Any suitable training scheme can be used.

In some cases, applying a machine learning model at block 312 can include supplying received data (e.g., sensor data such as flow signals and pressure signals) directly to the machine learning model. For example, inputs to a machine learning model can include a flow signal and a pressure signal. In some cases, however, applying the machine learning model at block 312 can include supplying features extracted from the received data. In such cases, identifying the user interface and/or conduit identification information can include determining features at block 310. Features can be determined in any suitable fashion, such as by analysis of sensor data using an algorithm or a machine learning model.

In some cases, determining features at block 310 can include determining one or more resonant frequencies associated with the fluid system comprising the flow generator, the conduit, and the user interface. Determining a resonant frequency can be performed in any suitable fashion, including applying a Cepstrum analysis to airflow parameters (e.g., the flow signal and/or pressure signal). Since different user interfaces and/or conduits can have different characteristics that result in different resonant frequencies being exhibited in the fluid system, one or more resonant frequencies associated with the fluid system can be a useful feature for identifying user interface and/or conduit identification information.

In some cases, determining features at block 310 can include determining a leak signal, such as an unintentional leak signal. The unintentional leak signal can be an indication of the presence of and/or intensity of any unintentional leaks over time during use of the user interface. Unintentional leaks can occur through insufficiently sealed portions of the user interface and/or conduit (e.g., between the user interface and the user or elsewhere, such as between the user interface and the conduit). The presence of and/or other information related to unintentional leaks can be indicative of type of user interface and/or conduit or other user interface and/or conduit identification information. For example, the type of unintentional leak that occurs when a user interface is removed can be different for full face user interfaces and nasal pillow user interfaces. In some cases, other information associated with the user's sleep session, such as sleeping position (e.g., supine, prone, left side, or right side), can be used with the unintentional leak signal to help determine user interface and/or conduit identification information. For example, certain user interfaces and/or conduits may be more likely to exhibit unintentional leaks in certain sleeping positions. As another example, certain user interfaces and/or conduits may make it less likely that a user would enter a particular sleeping position. For example, if no unintentional leak is detected yet it is detected that the user is sleeping in a prone sleeping position, it may be indicative that the user is not using a particular user interface (e.g., a full face user interface). Unintentional leaks do not include air intentionally escaping through one or more vents of the user interface and/or conduit.

In some cases, determining a leak signal can include determining an intentional leak signal. The intentional leak signal can be an indication of the presence of and/or intensity of any intentional leaks over time during use of the user interface. Intentional leaks can include airflow passing through one or more vents of the user interface and/or conduit or otherwise exiting the user interface and/or conduit in an intentional manner during application of respiratory therapy. The presence of and/or other information related to intentional leaks can be indicative of type of user interface and/or conduit or other user interface and/or conduit identification information. In some cases, other information associated with the user's sleep session, such as sleeping position (e.g., supine, prone, left side, or right side), can be used with the intentional leak signal to help determine user interface and/or conduit identification information. For example, certain sleeping positions may affect intentional leaks differently for different user interfaces (e.g., due to location and design of the vents and other features of the user interface) and/or conduits. For example, tube-up or top-of-head user interfaces may include vents that can be occluded in some sleeping positions, causing such user interfaces to exhibit different intentional leak signals than nasal pillow user interfaces.

In some cases, an intentional leak signal (e.g., an airflow passing through one or more vents of the user interface) can be characterized at different airflow parameters (e.g., at one or more therapy pressures). The changes in intentional leak signal at these different airflow parameters can be usable to identify user interface and/or conduit identification information. For example, different user interface and/or conduits can exhibit different characteristics with respect to how the user interface and/or conduit responds to changes airflow parameters (e.g., changes in flow rate or therapy pressure). As an example, a particular conduit may exhibit different pressure drops across the length of the conduit depending on the total flow rate, or in other words, the exhibited pressure drop is a function of the total flow rate through the conduit. That function can be different across different conduits, and thus can be a characteristic that is usable to differentiate the conduit from other conduits (e.g., to identify a style, model, and/or manufacturer of the conduit). Likewise, characteristic responses associated with a user interface (e.g., vents of a user interface) in response to changes in airflow parameters can be usable to differentiate that user interface from other user interfaces (e.g., to identify a style, model, and/or manufacturer of the user interface).

In some cases, determining features at block 310 can include determining a nasal-oral breathing signal. The nasal-oral breathing signal can be an indication, over time, of whether the user is breathing through their nose (e.g., nasal breathing), their mouth (e.g., oral breathing), or a combination thereof. Since different user interfaces and/or conduits may react differently to the presence of nasal breathing and/or oral breathing, or to changes between nasal breathing and oral breathing, a nasal-oral breathing signal can be a useful feature for identifying user interface and/or conduit identification information. For example, a characteristic flattening of the flow signal (e.g., flow waveform) during the expiration phase of breathing may indicate air escaping through the mouth, which would be indicative of the presence of a nasal mask or nasal pillow style user interface.

In some cases, determining features at block 310 can include determining a volumetric breathing signal. The volumetric breathing signal can be an indication, over time, of a volume of inhale and/or a volume of exhale. In some cases, a volumetric breathing signal can be a useful feature for identifying user interface and/or conduit identification information. For example, a volumetric breathing signal that shows greater volume of inhale than volume of exhale may indicate air escaping through the mouth, which would be indicative of the presence of a nasal mask or nasal pillow style user interface.

In some cases, determining features at block 310 can include determining a durational breathing signal. The durational breathing signal can be an indication, over time, of a duration of inhale and/or a duration of exhale. In some cases, a durational breathing signal can be a useful feature for identifying user interface and/or conduit identification information. The durational breathing signal can be useful as a feature for a machine learning model trained with training data containing durational breathing signals.

In some cases, determining features at block 310 can include determining one or more groupings of frequency components of airflow parameters (e.g., of the flow signal and/or of the pressure signal). A grouping of frequency components can include components of a signal that fall below, above, or within threshold frequencies. Frequency components can be represented as frequencies and intensities, such as through a time-domain-to-frequency-domain transform (e.g., a fast Fourier transform). One or more groupings of frequency components can be used as an input to a machine learning model or can be used to filter out undesirable data from one or more signals.

In some cases, determining one or more groupings of frequency components includes determining high frequency components, which can include components at or above a high-frequency threshold frequency. In some cases, high frequency components include components above a baseline respiration rate or other respiration rate threshold (e.g., a maximum respiration rate identified in current sensor data and/or historical sensor data, or a percentage above baseline respiration rate). Such high frequency components, also known as "AC" components due to its analogous meaning with alternating current, can relate to effects occurring rapidly, such as fluctuations due to rotation of the fan of the flow generator. In some cases, it can be desirable to remove high frequency components from a signal (e.g., a flow signal or pressure signal) when analyzing the signal to identify user interface and/or conduit identification information, since characteristics of user interfaces and/or conduits tend not to affect signals at high frequencies. In some cases, determining one or more groupings of frequency components can include determining non-high frequency components, or all frequency components that are not high frequency (e.g., all frequency components at or below the baseline respiration rate).

In some cases, determining one or more groupings of frequency components includes determining low frequency components, which can include components at or below a low-frequency threshold frequency. In some cases, low frequency components include components below a frequency that is slower than the baseline respiration rate or other respiration rate threshold (e.g., a minimum respiration rate identified in current sensor data and/or historical sensor data, or a percentage below such a respiration rate). For example, the low-frequency threshold may be at 0.5 Hz, 0.25 Hz, 0.125 Hz, 0.0625 Hz, or the like. Such low frequency components, also known as "DC" components due to its analogous meaning with direct current, can relate to slowly changing and/or steady-state effects, such as characteristics of the user interface and/or conduit (e.g., fluid impedance of the user interface and/or conduit). In some cases, an impedance signal can be determined from the low frequency components. In some cases, it can be desirable to use such low frequency components to identify user interface and/or conduit identification information, since characteristics of user interfaces and/or conduits tend to have the most effect at low frequencies.

In some cases, determining one or more groupings of frequency components includes determining middle frequency components, which can include components between a low-frequency threshold frequency (e.g., low-frequency threshold frequency as described above) and a high-frequency threshold frequency (e.g., baseline respiration rate). Such middle frequency components can relate to signals that change at moderate frequencies, which can include effects related to the user's use of the user interface and/or conduit. For example, breathing and movement of the user while the user is using the user interface, as well as the user interface's and/or conduit's response to such breathing and movement, may result in middle frequency components. In some cases, middle frequency components can be indicative of unintentional leaks in the user interface and/or conduit, and thus an unintentional leak signal can be determined from the middle frequency components in some cases. In some cases, it can be desirable to use such middle frequency components to identify user interface and/or conduit identification information, since characteristics of user interfaces and/or conduits tend to have an effect on such middle frequencies.

In some cases, identifying user interface and/or conduit identification information at block 306 can include identifying a transient event in the airflow parameters. Transient events can include removal and/or adjustment of the user interface and/or conduit, a change of position of the user while sleeping (e.g., moving between sleeping positions or shifting on a bed), a change in therapy pressure (e.g., a change in automatic positive airway pressure), or other such actions that result in a transient in an airflow parameter signal. The transient itself and/or the response to the transient can be used to help identify the user interface and/or conduit identification information. For example, different user interfaces and/or conduits may respond to a user donning the user interface and/or connecting the conduit in different, recognizable ways as detected in the airflow parameters. As another example, different user interfaces and/or conduits may respond differently to a user changing positions in a bed. For example, user interfaces with more substantial securing features (e.g., straps) and/or better seals than other user interfaces may behave differently before, during, and/or after a detected transient event, such as a detected change in a user's position on a bed. Such differences associated with a detected transient event can be useful in identifying user interface and/or conduit identification information.

In some cases, identifying user interface and/or conduit identification information at block 306 can include identifying a breath shape associated with a user's breath using the airflow parameters. The breath shape can be supplied to a machine learning model as input data (e.g., as an image file supplied to a convolutional neural network) or can be compared to template breath shapes. In some cases, a machine learning model can be trained on template breath shapes. One or more template breath shapes can be obtained for a number of different user interfaces and/or conduits, such that recognizable features of the breath shapes can be used to facilitate identification of the user interface and/or conduit based on the identified breath shape.

In some cases, identifying user interface and/or conduit identification information at block 306 can include requesting and receiving additional data at block 314. In some cases, additional data can be requested at block 314 when a determination is made that additional data is needed to select the correct user interface and/or conduit identification information from a pool of possible user interfaces and/or conduits. For example, if applying the machine learning model at block 312 resulted in determining only a style and/or manufacturer of user interface and/or conduit, the system may request additional information from the user to help further identify the model of user interface and/or conduit out of the pool of user interfaces and/or conduits matching the identified style and/or manufacturer. In some cases, additional data can be requested at block 314 when the user interface and/or conduit identification information is identified with a level of confidence below a threshold level. For example, if applying the machine learning model at block 312 resulted in identifying user interface and/or conduit identification information with a relatively low confidence level, the additional data can be requested to try and improve the confidence level and/or to merely confirm with the user that the identified user interface and/or conduit identification information is correct. Additional data can be requested from a user of the respiratory therapy system or another (e.g., a medical professional or a caretaker).

In some cases, requesting and receiving additional data at block 314 can include generating and presenting a confirmation request that indicates the most likely user interface and/or conduit identification information, then receiving a response to the confirmation request indicating that the most likely user interface and/or conduit identification information is correct or incorrect.

In some cases, requesting and receiving additional data at block 314 can include generating and presenting a request for purchase history information. In some cases, upon receiving approval to access purchase history information, such purchase history information can be used to facilitate identification of the user interface and/or conduit identification information. For example, if there are three possible user interfaces identified, but only one exists in the purchase history, the system may make select that user interface as the identified user interface. In other cases, other information associated with purchase history of the user interface and/or conduit (e.g., a receipt or photo of the resale packaging) may be provided in response to the request for purchase history information. In such cases, the purchase history information can be used to facilitated identification of the user interface and/or conduit identification information.

In some cases, requesting and receiving additional data at block 314 can include generating and presenting a request for additional sensor data, then receiving the additional sensor data and using the additional sensor data (similarly to using received sensor data from block 304) to identify user interface and/or conduit identification information. This additional sensor data can include audio data (e.g., an audio recording of air passing through the user interface and/or conduit), imaging data (e.g., a photograph, video, infrared image, LiDAR scan, thermal image, or other image of the user interface and/or conduit), and the like.

In some cases, requesting and receiving additional data at block 314 can include generating and presenting one or more questions to a user, then receiving response(s) to the question(s) and using the responses to facilitate identifying the user interface and/or conduit identification information. For example, the system can present the user with a series of questions, such as "Is your user interface in use?" or "Were you wearing your user interface between 11:00 pm and 11:30 pm last night?" or other such questions. The user can provide answers to the questions. Based on these answers, the process 300 can identify the user interface and/or conduit identification information. For example, an answer to the latter question about whether the user interface was in use during a particular time can help the system know how to analyze the sensor data, since sensor data acquired while the user interface was not being worn may be processed or interpreted differently than sensor data acquired while the user interface was being worn. Responses to questions can be used in other ways, as well.

In some cases, identifying user interface and/or conduit identification information at block 306 can include receiving historical data at block 316. Received historical data can include sensor data received at a previous instance of block 304, such as sensor data from a previous night, previous week, or other time. The historical data received at block 316 can relate to the same user associated with the received sensor data from block 304. The historical data can include airflow parameters, such as flow rate and pressure, as well as other data. The historical data can be used to facilitate processing and/or analysis of the received sensor data from block 304. For example, historical data can be used to identify a baseline breathing rate, which can be compared to the received sensor data at block 304 to identify changes in baseline breathing rate and/or to normalize received sensor data based on the baseline breathing rate identified from the historical data. In some cases, the historical data can include sensor data received in a previous sleep session, such as a sleep session beginning on a previous day. In some cases, the historical data can include sensor data received at least 24 hours prior to acquiring the sensor data receiving at block 304.

Identifying user interface identification information at block 306 can result in information usable to identify a characteristic of the user interface. In some cases, the user interface identification information is a style, model, or manufacturer of the user interface. This information can be used to identify one or more other characteristics of the user interface. For example, a particular model of user interface may exhibit a particular airflow impedance. In another example, a particular style of user interface (e.g., nasal pillow) may exhibit resonant frequencies that are different or not present in other styles of user interface (e.g., a facial mask), which can affect airflow through the user interface. Examples of characteristics that can be identified for a particular user interface can include style of the user interface; model of the user interface; manufacturer of the user interface; one or more resonant frequencies of the user interface; a fluid impedance of the user interface; a fluid resistance of the user interface; presence of, number of, and/or style of vents of the user interface; and/or other features or characteristics of the user interface.

Identifying conduit identification information at block 306 can result in information usable to identify a characteristic of the conduit connecting the user interface to the respiratory therapy device. In some cases, the conduit identification information is a style, model, or manufacturer of the conduit. This information can be used to identify one or more other characteristics of the conduit. For example, a particular model of conduit may exhibit a particular resistance to airflow. In another example, a particular style of conduit (e.g., heated conduit) may exhibit resonant frequencies that are different or not present in other styles of conduit (e.g., non-heated conduit), which can affect airflow through the conduit. Examples of characteristics that can be identified for a particular conduit can include style of the conduit; model of the conduit; manufacturer of the conduit; one or more resonant frequencies of the conduit; a fluid impedance of the conduit; a fluid resistance of the conduit; and/or other features or characteristics of the conduit.

In some cases, identifying user interface and/or conduit identification information at block 306 can include determining a confidence level associated with the identified user interface and/or conduit identification information. Such a confidence level can be represented as a number or percentage indicative of how certain the system is of the accuracy of the identified user interface and/or conduit identification information. In some cases, one or more confidence thresholds can be set to establish when certain actions described herein are taken. For example, as described above, a confidence level below a certain threshold can prompt the requesting and receiving of additional data at block 314. In another example, a confidence level above a certain threshold can be required before the generation of airflow is adjusted at block 320, as described in further detail below.

In some cases, flow generator identification information can be determined at optional block 308, separately, along with, or in addition to determining user interface and/or conduit identification information at block 306. Flow generator identification information can be determined at block 308 in the same or similar fashion to how user interface and/or conduit identification information is determined at block 306. For example, the same or a different machine learning model can be used to identify flow generator identification information from sensor data received at block 304. It will be understood that descriptions and examples for how user interface and/or conduit identification is determined as described herein can apply to flow generator identification information.

Identifying flow generator identification information at block 308 can result in information usable to identify a characteristic of the flow generator supplying the airflow to the user interface. In some cases, the flow generator identification information is a style, model, or manufacturer of the flow generator. This information can be used to identify one or more other characteristics of the flow generator. For example, a particular model of flow generator may exhibit a particular pattern of high frequency components in an airflow parameter signal. Examples of characteristics that can be identified for a particular flow generator can include style of the flow generator; model of the flow generator; manufacturer of the flow generator; one or more resonant frequencies of the flow generator; and/or other features or characteristics of the flow generator. As described above with reference to identifying user interface and/or conduit identification information at block 306, identifying flow generator identification information at block 308 can include determining features and applying a machine learning model, similar to determining features at block 310 and applying a machine learning model at block 312; requesting and receiving additional data, similar to requesting and receiving additional data at block 314; receiving historical data, similar to receiving historical data at block 316; or any combination thereof.

At block 318 the user interface and/or conduit identification information from block 306, as well as optionally the flow generator identification information from block 308, can be leveraged. Leveraging this identification information can be used to perform one or more actions, such as adjusting generation of airflow at block 320, presenting user interface and/or conduit identification at block 322, and/or generating a notification at block 324.

At block 320, generation of airflow through the user interface can be adjusted based on the identified user interface and/or conduit identification information from block 320. Adjusting generation of airflow at block 320 can include adjusting one or more settings of the respiratory device to cause future airflow to be generated in a different manner than at block 302. For example, adjusting generation of airflow can include driving a motor of a flow generator at a different speed or different pattern of speeds. In some cases, adjusting generation of airflow at block 320 can make use of the airflow parameters, either via using the identification of the user interface and/or conduit identification information obtained from the airflow parameters or in addition to using the user interface and/or conduit identification information. In some cases, adjusting generation of airflow at block 320 includes determining that the identified user interface and/or conduit identification information is different than existing user interface and/or conduit identification information (e.g., previously stored or previously set user interface and/or conduit identification information stored in the system).

At block 322, the user interface and/or conduit identification information can be presented, such as to the user, to a caregiver, or otherwise. Presenting the user interface and/or conduit identification information can include sending a transmission to an external device such that the external device, upon receiving the transmission, generates a display, on a graphical user interface, based on the user interface and/or conduit identification information. For example, the system can send a transmission containing a model of the user interface and/or conduit as identified at block 306. Upon receiving the transmission, the external device can generate a display indicating the model of the user interface and/or conduit. In some cases, the display can be informative in nature, such as to show the correct model of user interface and/or conduit in a graphical display, to show the correct donning instructions for wearing the user interface based on the model of the user interface, to show the correct connection instructions for connecting the conduit based on the model of the conduit, or to warn the user or caregiver that the detected user interface and/or conduit is not the same as the user interface and/or conduit that is expected (e.g., as compared to an existing setting of the respiratory device). In some cases, the display can be a prompt that requests confirmation from the user, which confirmation can be used to implement other actions (e.g., adjust generation of airflow) and/or further train the machine learning model.

At block 324, a notification can be generated based on the user interface and/or conduit identification information (and/or other identification information). The notification can be any suitable notification, such as a notification that the user interface and/or conduit detected does not align with an expected user interface and/or conduit. For example, the system can access a stored setting in the system (e.g., existing user interface and/or conduit identification information) that indicates the user interface and/or conduit that is intended to be used with the system (e.g., such as previously been determined or previously set), then compare this stored setting with the user interface and/or conduit identification information identified at block 306. If the user interface and/or conduit does not match as determined by this comparison, a notification can be generated to inform the user so the user can take any action that may be necessary, such as switching settings on the system or switching out the user interface and/or conduit.

Process 300 is depicted with a certain arrangement of blocks, however in other cases, these blocks can be performed in different orders, with additional blocks, and/or some blocks removed.

Figure 4:
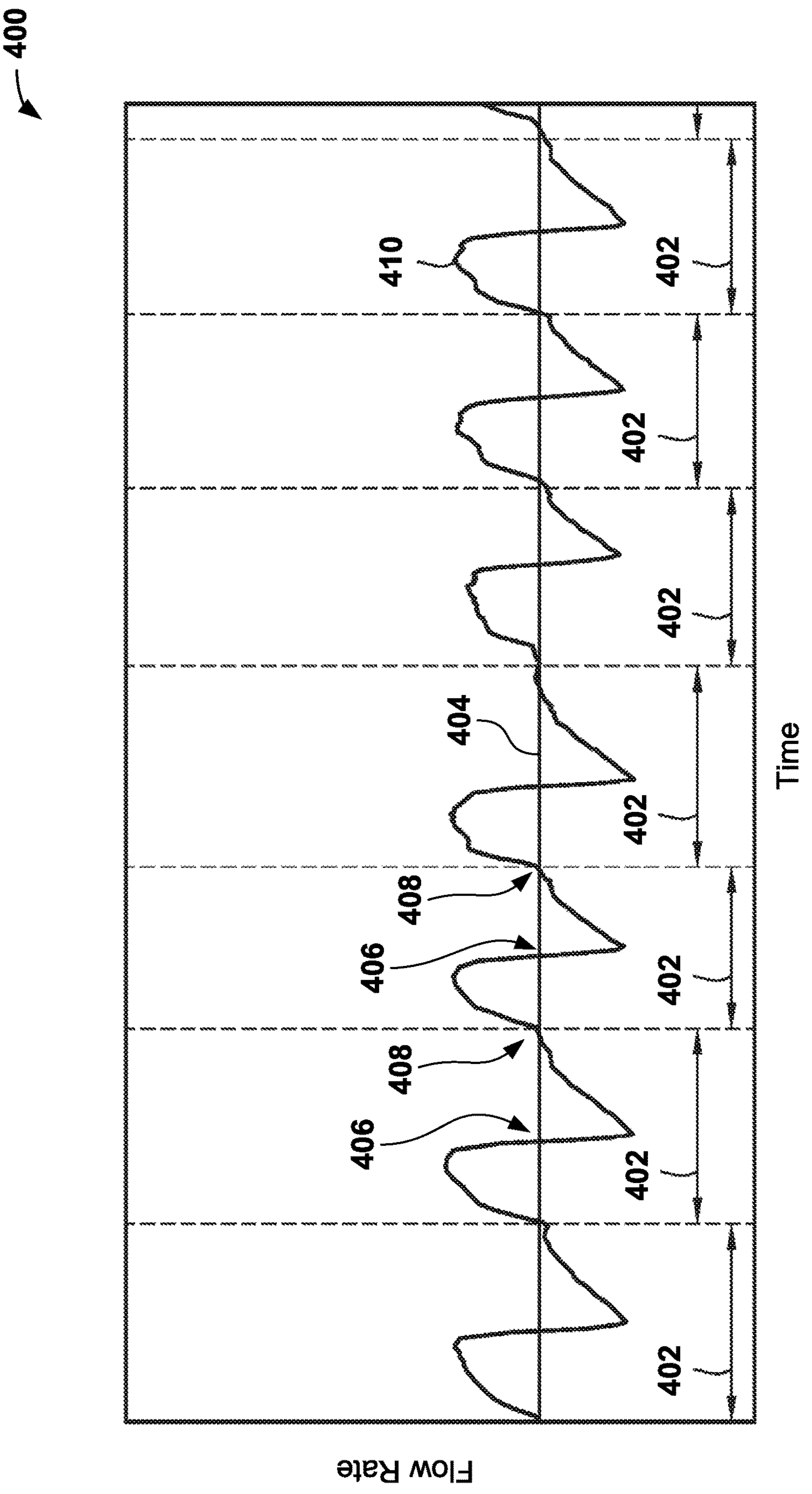
FIG. 4 is a chart depicting an example flow rate signal that may be used to identify user interface identification information, according to certain aspects of the present disclosure.

FIG. 4 is a chart 400 depicting an example flow rate signal 410 that may be used to identify user interface and/or conduit identification information, according to certain aspects of the present disclosure. Flow rate signal 410 is a representation of flow rate (y-axis) as a function of time (x-axis) as a user is making use of the respiratory therapy system, such as during a sleep session. Flow rate signal 410 can be obtained through one or more sensors, such as flow rate sensor 134 of FIG. 1.

Flow rate signal 410 shows a repetitive pattern representing repeating breathing cycles 402. Line 404 can represent a nominal flow rate or a zero flow rate. As the user breaths in the flow rate signal 410 is above line 404. As the user breaths out, the flow rate signal 410 is below line 404. Thus, a single exhale can extend from an end of inhale point 406 to an end of exhale point 408 within each breathing cycle 402. Likewise, a single inhale can extend from an end of exhale point 408 to an end of inhale point 406. Thus, the volume of a single inhale can be the area between line 404 and the flow rate signal 410 between an exhale point 408 and an inhale point 406. Likewise, the volume of a single exhale can be the area between line 404 and the flow rate signal 410 between an inhale point 406 and an exhale point 408.

Various features can be extracted from the flow rate signal 410, such as described with reference to determining features at block 310 of FIG. 3. For example, the flow rate signal 410 can be used to determine a minimum flow rate, a maximum flow rate, an area of one or both breathing phases (e.g., inspiration and expiration), a rise time (e.g., time from minimum flow to zero and/or a time from zero to peak flow), a fall time (e.g., a time from maximum flow to zero and/or a time from zero to minimum flow), a ratio between other features (e.g., ratio of rise time to fall time or ratio of inspiration area to expiration area), skewness present in the flow rate signal 410, kurtosis of any section of the flow rate signal 410, and others. In some cases, features can be extracted from the flow rate signal 410 by analyzing a first derivative and/or second derivative of the flow rate signal 410, such as to more easily analyze rate of change of the signal.

As disclosed herein, such as with reference to FIG. 3, the flow rate signal 410 can be used to identify user interface and/or conduit identification information. In some cases, data from the flow rate signal 410 can be applied to a machine learning algorithm directly, or can used to extract features usable as inputs to a machine learning algorithm. For example, a graphical depiction of a portion of the flow rate signal 410 and/or a spectrogram of a portion of the flow rate signal 410 can be used as input to a convolutional neural network to facilitate identification of the user interface and/or conduit identification information.

Figure 5:
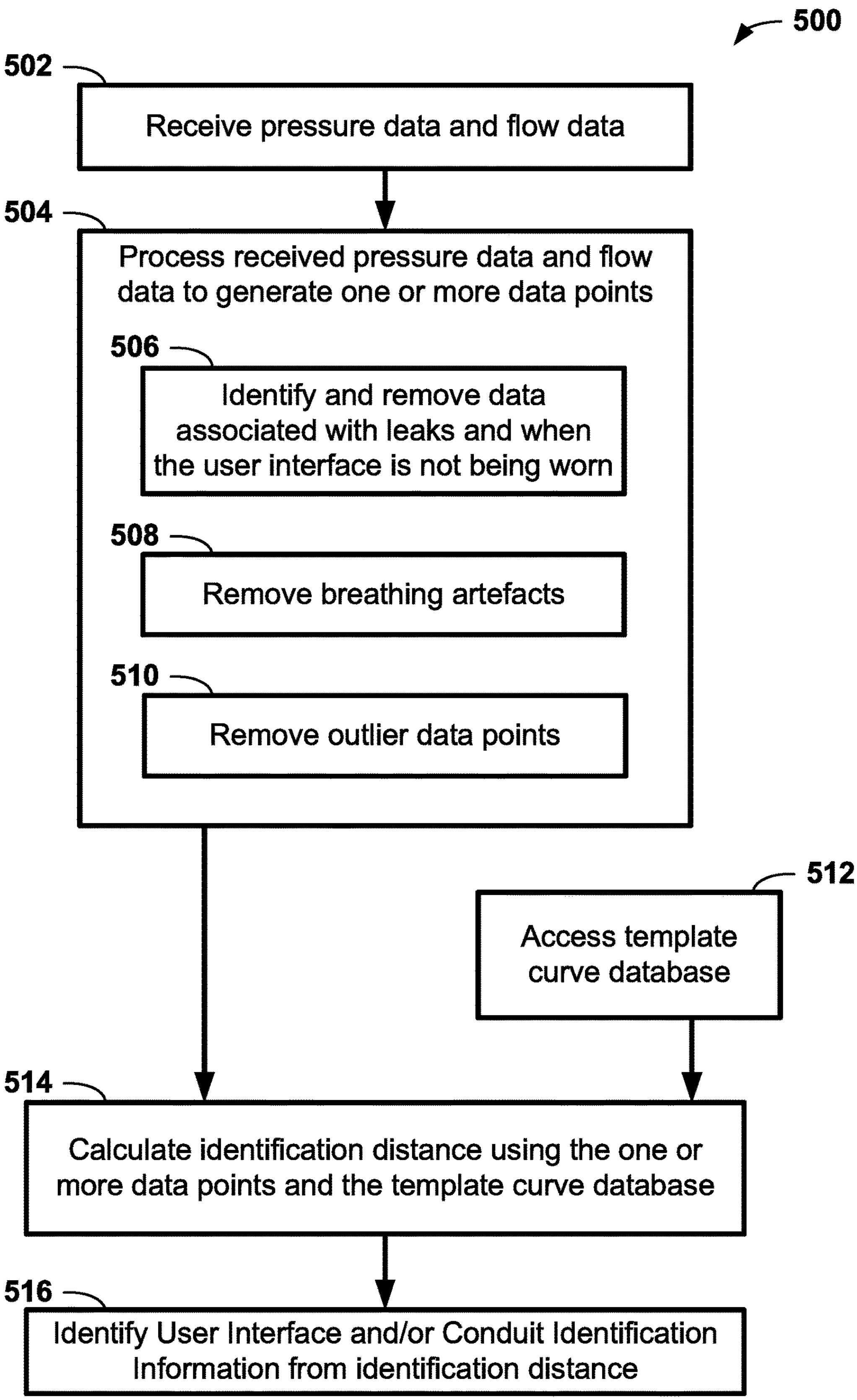
FIG. 5 is a flowchart depicting a process for analyzing pressure data and flow data to determine user interface and/or conduit identification information, according to certain aspects of the present disclosure.

FIG. 5 is a flowchart depicting a process 500 for analyzing pressure data and flow data to determine user interface and/or conduit identification information, according to certain aspects of the present disclosure. Process 500 can be performed on any suitable system, such as on control system 110 of system 100 of FIG. 1. In some cases, process 500 can be performed as part of process 300 of FIG. 3, such as incorporated as part of block 306 of FIG. 3. In some cases, process 500 can be performed in realtime, although that need not always be the case.

At block 502, pressure data and flow data are received. Pressure data and flow data can be pressure data and flow data acquired by a flow generator (e.g., blower pressure and blower flow, respectively), and can be presented in any appropriate units (e.g., $cmH_2O$ for pressure data and L/min for flow data). In some cases, pressure data and/or flow (e.g., flow rate) data can be received as a time-dependent stream of data (e.g., a pressure signal and a flow signal).

At block 504, the pressure data and flow data are processed to generate one or more data points. Each data point can include a pressure value and a corresponding flow rate value at a given point in time. The number of data points generated can depend at least in part on the duration of the therapy session being processed and the sampling rate. For example, a ten-minute session with a sampling rate of 10 Hz can result in 6,000 data points. The one or more data points generated at block 504 can be a point cloud. If desired, such a point cloud can be visualized on a two-dimensional histogram (e.g., a 2D histogram with flow on the X axis and pressure on the Y axis). As used herein, the term point cloud can include a collection of data points (e.g., data points each including a pressure value and a corresponding flow rate value for a given point in time).

In some cases, processing the received pressure data and flow data can include, at block 506, identifying and removing data (e.g., pressure data and flow data) associated with unintentional leaks and/or the user interface not being worn by a user. Identifying data associated with unintentional leaks can include identifying one or more time durations in which an unintentional leak is occurring. Removing the data associated with the unintentional leaks can include excluding any pressure data and flow data, or excluding data points, that are associated with each identified time duration in which an unintentional leak is occurring. Identifying data associated with a user interface not being worn by a user can include identifying one or more time durations in which the user interface is determined to be not worn by the user. Removing the data associated with the user interface not being worn by the user can include excluding any pressure data and flow data, or excluding data points, that are associated with that time duration in which the user interface is determined to be not worn by the user.

In some cases, processing the received pressure data and flow data can include removing breathing artefacts at block 508. Removing breathing artefacts can include filtering the received pressure data and flow data to remove information or artefacts that are attributable to the user's breath. In some cases, removing breathing artefacts can include applying a low pass filter to each of the received pressure data and the flow data (e.g., applying the filter to the pressure signal and the flow signal). This low pass filter can include applying a mean filter over a time duration, such as a duration of 30 seconds to 1 minute. In some cases, removing breathing artefacts can include filtering the received pressure data and flow data according to a breath phase analysis. For example, in some cases, breathing artefacts can be removed by selectively removing all data points that are associated with transitional phases of the user's breath (e.g., while inhaling or exhaling). Thus, the only remaining data points would be those associated with steady-state phases of the user's breath (e.g., the steady states between inhaling and exhaling). In some cases, removing breathing artefacts can include removing artefacts due to intentional leaks. Any suitable techniques for detecting unintentional leaks, intentional leaks, and/or breathing phases can be used, such as those described herein and/or those described with reference to WO 2021/176426, which is hereby incorporated by reference herein in its entirety.

In some cases, processing the received pressure data and flow data can include removing outlier data points at block 510. Removing outlier data points can include identifying and removing data points having a frequency of occurrence below a threshold frequency of occurrence over a duration of time. In some cases, the duration of time can be a session during which the received pressure data and flow data is received (e.g., a full sleep session, all data collected since the respiratory device was turned on, or all data collected since the user interface was coupled to the respiratory device). In some cases, such as when process 500 is being performed in realtime, the duration of time can be a previous duration of time, such as the past two minutes. In some cases, the duration of time can be across multiple sessions of receiving pressure data and flow data (e.g., multiple different sessions representative of multiple uses of respiratory therapy across multiple nights). In some cases, removing outlier data points can include identifying and removing data points having a frequency of occurrence below a threshold frequency of occurrence over a preset number of previous data points. Any suitable threshold frequency of occurrence can be used, such as 1% of the session duration.

In some cases, for each of the pressure data (e.g., pressure signal) and flow data (e.g., flow signal), block 504 can include initially performing block 506 on received signal to generate a pre-filter signal, which can be passed to block 508 to generate a filtered signal. The filtered signals can then be used to generate a set of data points, which can then be passed to block 510 to remove outliers from the set of data points, resulting in a set of one or more data points. In some cases, one or more of blocks 506, 508, and 510 can be removed or performed in a different order.

At block 512, a template curve database is accessed. The template curve database can be stored locally or remotely (e.g., on the Cloud or on a remote server). The template curve database can be a collection of one or more template curves used in the comparison of pressure data and flow data. In some cases, a single template curve is used. In some cases, multiple template curves can be used, such as a different template curve for each different style of user interface (e.g., full face, nasal, nasal pillow).

Each template curve can be a pressure-versus-flow curve indicating a certain relationship of pressure versus flow for a fluid system. In some cases, a template curve can be a prophetic template curve, in which case the template curve is specifically generated to ensure a high degree of differentiability between different types of user interface identification information and/or conduit identification information. For example, a prophetic template curve can be a curve that has been found to work especially well at differentiating the different styles of user interface. In another example, a prophetic template curve can be a curve that has been found to work especially well at differentiating different models of user interface (e.g., certain commonly used models).

In some cases, however, a template curve can be based on actual, controlled measurements from different user interfaces and/or conduits. For example, a database of template curves can be generated for a number of user interfaces of different styles, of different models, or having other differences. Such a database can be generated by acquiring pressure data and flow data during controlled experiments (e.g., coupling the user interface to a face model and measuring pressure data and flow data while controlling the flow generator).

In some cases, each template curve in the template curve database can be associated with a unique user interface (e.g., a unique user interface style and/or a unique user interface model), a unique conduit (e.g., a unique conduit style and/or a conduit model), or a unique user interface and conduit combination (e.g., a unique user interface style and/or a unique user interface model in combination with (e.g., coupled to) a unique conduit style and/or a unique conduit model).

At block 514, an identification distance can be calculated based at least in part on the one or more data points from block 504 and the template curve database at block 512. The identification distance is a comparison of the one or more data points to one or more of the template curves from the template curve database. As described in further detail herein, an identification distance can be a useful calculation for identifying a user interface and/or conduit, since different user interfaces and different conduits can produce recognizable identification distances. In some cases, a single template curve can be used and different user interfaces and/or conduits can be differentiated by their different identification distances. In some cases, multiple unique template curves can be used, and different user interfaces and/or conduits can be differentiated by identifying which of the unique template curves results in the smallest identification distance.

In some cases, a single template curve is used to calculate an identification distance at block 514, although that need not always be the case. Calculating an identification distance can include calculating, for each data point, one or more distances from the data point to the template curve.

A flow-based distance ($\Delta Q$) can be a distance between the data point and the template curve at a given pressure level, such as $\Delta Q=Q-Q_0$, where Q is the flow rate of the data point and $Q_0$ is the flow rate of the template curve at the pressure value of the data point.

A pressure-based distance ($\Delta P$) can be a distance between the data point and the template curve at a given flow rate, such as $\Delta P=P-P_0$, where P is the pressure at the data point and $P_0$ is the pressure of the template curve at the flow rate of the data point (e.g., $P_0=aQ_0^2+bQ_0+c$, where a, b, and c are constants).

A minimum distance to curve ($\tilde{p}$) can be calculated. The minimum distance to curve can take into account offsets in both pressure and flow rate. A non-dimensionalization of the pressure and flow values can be first performed, since pressure and flow can have different magnitudes which can skew a minimum distance to curve measurement). A reference pressure value ($P_R$) and a reference flow rate ($Q_R$) can be preset (e.g., 10 $cmH_2O$ and 0.5 L/s, respectively). The non-dimensionalized flow value be $$\tilde{Q} = \frac{Q}{Q_R}$$

and the non-dimensionalized pressure value can be $$\tilde{P} = \frac{P}{P_R}.$$

The non-dimensionalized curve is thus $$\bar{p} = \frac{aQ_R^2}{P_R}\bar{q}^2 + \frac{bQ_R}{P_R}\bar{q} + \frac{C}{P_R}.$$

The minimum distance between the data point and that curve can be calculated.

In some cases, the identification distance can be based on a flow-based distance, a pressure-based distance, a minimum distance to curve, or any combination thereof. When a single data point is being analyzed, the identification distance can be the distance(s) (e.g., flow-based distance, pressure-based distance, minimum distance to curve, or any combination thereof) for that data point. However, when multiple data points are used, the distance(s) for each data point can be used to calculate the identification distance in an equal and/or weighted fashion.

In some cases, the distance(s) calculated for each data point can be sum weighted based on the frequency of occurrence of that data point. In some cases, the distance(s) calculated for each data point can be sum weighted based on pressure levels, such as by providing greater weight to higher pressures and/or providing greater weights to pressures of the template curve known to be a more reliable approximation for the behavior of the system. In some cases, since blocking of a conduit can result in a negative flow rate offset with respect to the template curve, the distance(s) calculated for each data point can be sum weighted based on flow rate, such as by providing greater weight to greater flow rates for a given pressure bin (e.g., a given pressure level or range of pressure levels). In some cases, comparing the multiple data points can include any suitable combination of the aforementioned techniques, as well as variations thereof.

In some case, calculating the identification distance at block 514 can further include generating a level of confidence associated with the identification distance. Generating a level of confidence can include calculating an amount of scatter (e.g., variability or dispersion) associated with the data points. The level of confidence can be based at least on the amount of scatter. For example, when data points are collected that vary widely along the flow and pressure axes, it can be assumed that the identification distance, and thus the resultant identification, will have a relatively low level of confidence. However, if the data points have little variation along the flow and pressure axes, it can be assumed that the identification distance, and thus the resultant identification, will have a relatively high level of confidence.

At block 516, the identification distance calculated at block 514 can be used to identify user interface and/or conduit identification information. The identification distance can be compared with a lookup table, can be applied to a formula, or can be otherwise classified (e.g., supplied to a pre-trained machine learning classifier) to generate the user interface and/or conduit identification information. The user interface identification information and conduit identification information can be similar to that identified at block 306 of FIG. 3.

Certain aspects and features of the present disclosure are described with reference to pressure data and flow data, such as data points containing pressure values and flow rate values, as well as template curves used to compare pressure data and flow data. However, knowledge of impedance (i.e., Z, which may be calculated as P/Q) and one of pressure data and flow data can be used to ascertain the other of pressure data and flow data. Thus, as used herein, such as with reference to process 500, either pressure data or flow data can be replaced with impedance data to achieve suitably similar embodiments. For example, instead of receiving pressure data and flow data at block 502, pressure data and impedance data can be received. In such an example, any template curve used to calculate the identification distance can be a pressure-versus-impedance curve instead of a pressure-versus-flow curve. Likewise, if flow data and impedance data is received, the template curve(s) can be flow-versus-impedance curve(s).

Process 500 is depicted with a certain arrangement of blocks, however in other cases, these blocks can be performed in different orders, with additional blocks, and/or some blocks removed. For example, in some cases, process 500 begins by generating airflow through a user interface, similar to block 302 of FIG. 3, before receiving the pressure data and flow data at block 502. As another example, in some cases, process 500 continues by leveraging user interface and/or conduit identification information, similar to block 318 of FIG. 3, after identifying the user interface and/or conduit identification information at block 516.

Figure 6:
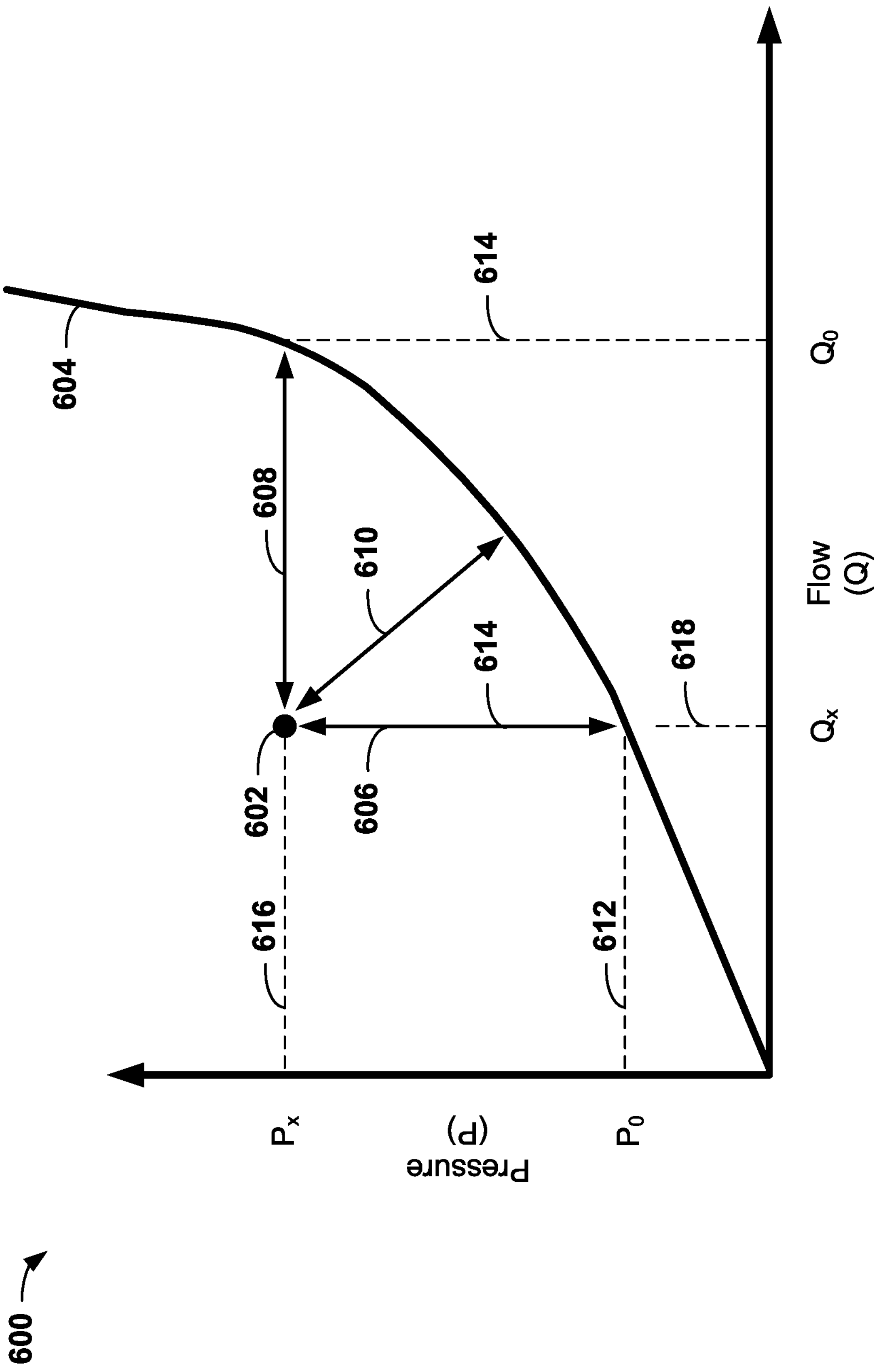
FIG. 6 is an example chart depicting a data point being compared with a template curve, according to certain aspects of the present disclosure.

FIG. 6 is an example chart 600 depicting a data point 602 being compared with a template curve 604, according to certain aspects of the present disclosure. The data point 602 can be any of the one or more data points generated at block 504 of FIG. 5. The template curve 604 can be any suitable template curve, such as a template curve of a template curve database, such as the template curve database accessed at block 512 of FIG. 5.

The flow-based distance 608 is a distance between the data point 602 and the template curve 604 at a given pressure level (e.g., the pressure level 616 of the data point 602). The template flow rate at the given pressure level can be denoted $Q_0$ 614.

The pressure-based distance 606 is a distance between the data point 602 and the template curve 604 at the given flow rate (e.g., the flow rate 618 of the data point 602). The template pressure level at the given flow rate can be denoted $P_0$ 612.

The minimum distance to curve 610 is the distance between the data point 602 and the closest point on the template curve 604 to the data point 602.

Figure 7:
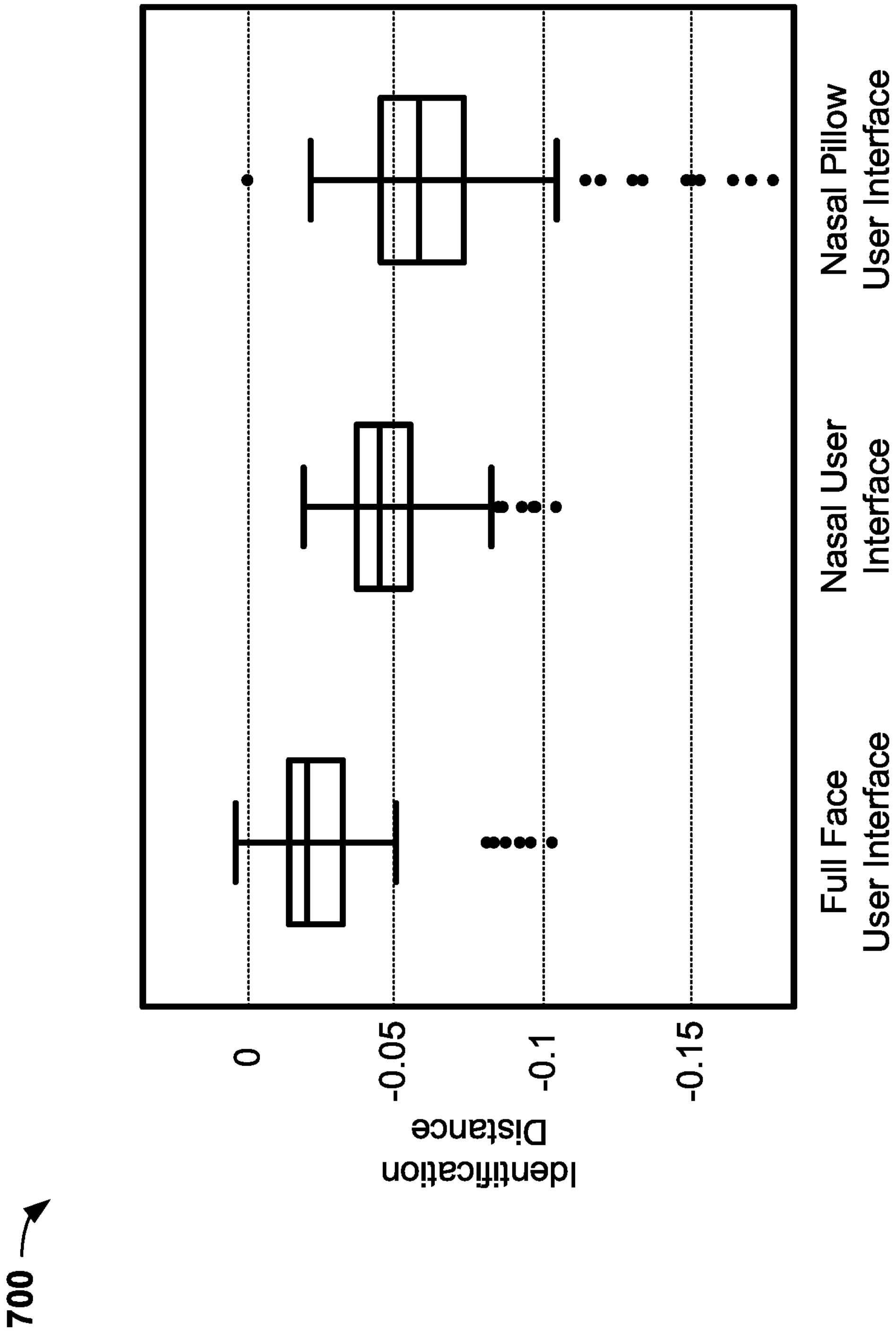
FIG. 7 is an example chart depicting experimental data for identification distance across multiple styles of user interface, according to certain aspects of the present disclosure.

FIG. 7 is an example chart 700 depicting experimental data for identification distance across multiple styles of user interface, according to certain aspects of the present disclosure. The identification distances of FIG. 7 can be dimensionless. The sign of the identification distance can indicate whether the data point is to the left or right of the template curve (e.g., a negative identification distance can indicate the data point is to the left of the template curve), although in some cases the identification distance can be signless.

The data for chart 700 was acquired for 53 different patients across seven nights each. Each of the patients used a full face user interface, a nasal user interface, or a nasal pillow user interface. The resultant identification distances associated with full face user interfaces, nasal user interfaces, and nasal pillow user interfaces were easily distinguishable from one another. In other words, chart 700 shows that there is good separation between full face user interfaces, nasal user interfaces, and nasal pillow user interfaces.

One or more elements or aspects or steps, or any portion(s) thereof, from one or more of any of the claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular aspects or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:

generating airflow through a user interface, wherein generating the airflow includes generating the airflow using a flow generator;

measuring one or more airflow parameters associated with the generated airflow, wherein the one or more airflow parameters include at least one of a flow signal of the generated airflow and a pressure signal of the generated airflow;

identifying user interface identification information based on the measured one or more airflow parameters, wherein the user interface identification information is usable to identify a characteristic of the user interface;

receiving stored existing user interface identification information associated with the flow generator from a storage device;

comparing the stored existing user interface identification information with the identified user interface identification information;

determining that the identified user interface identification information is different than the existing user interface identification information; and generating a notification in response to determining that the identified user interface identification information is different than the existing user interface identification information.

2. The method of claim 1, further comprising determining an adjustment to the generation of the airflow through the user interface based on the identified user interface identification information.

3. The method of claim 1, wherein the user interface identification information includes at least one of a manufacturer of the user interface, a model of the user interface, and a style of the user interface.

4. The method of claim 1, wherein the one or more airflow parameters includes a flow signal, wherein the flow signal includes first flow data captured while the user interface is not worn by a user and second flow data captured while the user interface is worn by the user, and wherein identifying the user interface identification information is based on the first flow data and the second flow data.

5. The method of claim 1, further comprising:

determining a need for additional data associated with the user interface;

generating a prompt requesting the additional data; and receiving the additional data in response to the prompt;

wherein identifying the user interface identification information is further based on the additional data, and wherein the additional data includes (i) audio data associated with the airflow through the user interface, (ii) imaging data associated with an image of the user interface, (iii) one or more responses to one or more questions about the user interface, or (iv) any combination of (i) to (iii).

6. The method of claim 1, wherein identifying user interface identification information includes:

determining one or more features based on the measured one or more airflow parameters; and applying the determined one or more features as inputs to a machine learning model, wherein output of the machine learning model is usable to determine the user interface identification information;

wherein determining the one or more features includes:

generating one or more data points based at least in part on the one or more airflow parameters, wherein each of the one or more data points includes a pressure value and a corresponding flow value;

accessing one or more template curves; and generating a comparison of the one or more data points with the one or more template curves, wherein the one or more features includes the comparison.

7. The method of claim 6, wherein generating the comparison includes calculating an identification distance between the one or more data points and the one or more template curves, wherein calculating the identification distance includes i) calculating a minimum distance between the one or more data points and the one or more template curves; ii) calculating a flow-based distance between the one or more data points and the one or more template curves; iii) calculating a pressure-based distance between the one or more data points and the one or more template curves; or iv) any combination of i-iii.

8. The method of claim 6, wherein the one or more features includes a resonant frequency signal associated with the user interface, wherein the resonant frequency signal is indicative of one or more resonant frequencies associated with the user interface over time.

9. The method of claim 6, wherein the one or more features includes:

(i) an unintentional leak signal associated with the user interface, wherein the unintentional leak signal is indicative of one or more unintentional leaks associated with the user interface over time;

(ii) a nasal-oral breathing signal associated with the user interface, wherein the nasal-oral breathing signal is indicative of nasal breathing or oral breathing associated with the user interface over time;

(iii) a volumetric breathing signal associated with the user interface, wherein the volumetric breathing signal is indicative of at least one of a volume of inhale and a volume of exhale over time; or (iv) any combination of (i) to (iii).

10. The method of claim 6, wherein determining the one or more features:

(i) uses high frequency components of the measured one or more airflow parameters, and wherein determining the one or more features includes:

identifying a baseline respiration rate based on the measured one or more airflow parameters; and identifying the high frequency components of the measured one or more airflow parameters, wherein the high frequency components occur at frequencies above the baseline respiration rate;

(ii) uses non-high frequency components of the measured one or more airflow parameters, and wherein determining the one or more features includes:

identifying a baseline respiration rate based on the measured one or more airflow parameters; and identifying the non-high frequency components of the measured one or more airflow parameters, wherein the non-high frequency components occur at frequencies below the baseline respiration rate;

(iii) uses middle frequency components of the measured one or more airflow parameters, and wherein determining the one or more features includes:

identifying a baseline respiration rate based on the measured one or more airflow parameters; and identifying the middle frequency components of the measured one or more airflow parameters, wherein the middle frequency components occur at frequencies below the baseline respiration rate and above a low-frequency threshold frequency, wherein determining the one or more features further includes determining an unintentional leak signal associated with the user interface using the middle frequency components, wherein the unintentional leak signal is indicative of one or more unintentional leaks associated with the user interface over time;

(iv) uses low frequency components of the measured one or more airflow parameters, and wherein determining the one or more features includes identifying the low frequency components of the measured one or more airflow parameters, wherein the low frequency components occur at frequencies below a low-frequency threshold frequency; or (v) any combination of (i) to (iv).

11. The method of claim 1, wherein generating the airflow includes generating the airflow using a flow generator, wherein the method further comprises receiving flow generator parameters associated with the flow generator, and wherein identifying the user interface identification information is further based on the flow generator parameters.

12. The method of claim 1, wherein identifying the user interface identification information includes:

generating a spectrogram using the measured one or more airflow parameters; and applying the spectrogram to a deep neural network to determine the user interface identification information.

13. The method of claim 1, wherein generating the airflow includes generating a known adjustment to the airflow and reverting the known adjustment to the airflow, wherein measuring the one or more airflow parameters occur before and after the known adjustment, and wherein identifying the user interface identification information is based on changes in the measured one or more airflow parameters associated with the known adjustment.

14. The method of claim 1, wherein measuring the one or more airflow parameters occur during a transient event, wherein the transient event includes removing the user interface or donning the user interface.

15. The method of claim 1, further comprising updating a setting of the flow generator in response to determining that the identified user interface identification information is different than the existing user interface identification information.

16. The method of claim 1, wherein generating the airflow includes generating the airflow using a flow generator, the method further comprising identifying flow generator identification information based on the flow signal and the pressure signal.

17. The method of claim 1, wherein measuring the one or more airflow parameters includes:

measuring pressure data associated with the generated airflow and flow data associated with the generated airflow; and generating one or more data points based at least in part on the pressure data and the flow data, wherein the one or more data points includes a pressure value and a corresponding flow value; and wherein a conduit couples the flow generator to the user interface, and wherein identifying the user interface identification information includes:

accessing one or more template curves;

generating a comparison of the one or more data points with the one or more template curves; and identifying at least one of the user interface identification information and conduit identification information of the conduit based at least in part on the comparison, wherein the conduit identification information is usable to identify a characteristic of the conduit.

18. A system comprising:

a control system including one or more processors; and a memory having stored thereon machine readable instructions;

wherein the control system is coupled to the memory, and the method of claim 1 is implemented when the machine executable instructions in the memory are executed by at least one of the one or more processors of the control system.

19. A computer program product, embodied in a non-transitory computer readable medium, comprising instructions which, when executed by a computer, cause the computer to carry out the method of claim 1.

20. The method of claim 1, wherein identifying the user interface identification information based on the measured one or more airflow parameters includes:

determining spectral components of the one or more airflow parameters; and determining a shape feature and/or a size feature of the user interface based on the spectral components.

21. The method of claim 1, further comprising:

determining a confidence level associated with the identified user interface identification information;

comparing the confidence level with a threshold value;

in response to the confidence level being below a threshold level, determining a need for additional data associated with the user interface; and requesting the additional data associated with the user interface.

* * * * *